United States Patent [19]

Luderer

[11] 4,425,427

[45] Jan. 10, 1984

[54] SIMULTANEOUS, KINETIC, SPECTROPHOTOMETRIC ANALYSIS OF BLOOD SERUM FOR MULTIPLE COMPONENTS

[75] Inventor: Thomas K. J. Luderer, BR Dieren, Netherlands

[73] Assignee: Vitafin N.V., Curacao, Netherlands Antilles

[21] Appl. No.: 198,796

[22] Filed: Oct. 20, 1980

Related U.S. Application Data

[63] Continuation-in-part of Ser. No. 130,078, Mar. 13, 1980, abandoned, which is a continuation of Ser. No. 12,859, Feb. 16, 1979, abandoned.

[51] Int. Cl.$^3$ .................... G01N 33/52; G01N 33/62; G01N 33/66; G01N 33/68
[52] U.S. Cl. ........................................ 435/10; 422/61; 435/4; 435/11; 435/12; 435/14; 435/15; 435/16; 435/20; 435/26; 435/27; 435/810; 436/34; 436/74; 436/79; 436/86; 436/88; 436/95; 436/108
[58] Field of Search .................... 23/230 R, 230 B; 435/11, 4, 12, 14, 15, 16, 20, 26, 27, 810; 436/34, 74, 79, 86, 88, 95, 108; 422/61

[56] References Cited

U.S. PATENT DOCUMENTS

| | | | |
|---|---|---|---|
| 2,951,090 | 8/1960 | Ujejski et al. | 260/534 |
| 3,290,228 | 12/1966 | Gretton | 195/127 |
| 3,334,069 | 8/1967 | Wachter | 195/103.5 |
| 3,413,198 | 11/1968 | Deutsch | 195/103.5 |
| 3,607,093 | 9/1971 | Stone | 23/253 |
| 3,653,836 | 4/1972 | Gruber et al. | 23/230 B |
| 3,703,441 | 11/1972 | Nakanishi et al. | 195/99 |
| 3,703,591 | 11/1972 | Bucolo et al. | 195/103.5 R |
| 3,718,433 | 2/1973 | Emmet | 23/230 R |
| 3,739,013 | 6/1973 | Picciola et al. | 260/471 R |
| 3,759,793 | 9/1973 | Stork et al. | 195/103.5 R |
| 3,764,478 | 10/1973 | Bergmeyer et al. | 195/99 |
| 3,773,626 | 11/1973 | Bernt et al. | 195/103.5 R |
| 3,776,816 | 12/1973 | Terada et al. | 195/66 R |
| 3,791,931 | 2/1974 | Thum et al. | 195/103.5 R |
| 3,803,223 | 4/1974 | Mazur et al. | 260/534 R |
| 3,862,009 | 1/1975 | Wahlefeld et al. | 195/103.5 R |
| 3,869,348 | 3/1975 | Gindler | 195/99 |
| 3,884,637 | 5/1975 | Gindler | 23/230 B |
| 3,892,631 | 7/1975 | Carroll | 195/99 |
| 3,894,844 | 7/1975 | Pinto et al. | 23/230 B |
| 3,899,297 | 8/1975 | Hirschfeld | 23/230 |
| 3,907,645 | 9/1975 | Richmond | 195/99 |
| 3,915,643 | 10/1975 | Gindler | 23/230 B |
| 3,925,162 | 12/1975 | Kanno | 195/103.5 R |
| 3,925,164 | 12/1975 | Beaucamp et al. | 195/103.5 R |
| 3,926,736 | 12/1975 | Bucolo | 195/103.5 R |
| 3,953,297 | 4/1976 | Gindler | 195/103.5 R |
| 3,953,359 | 4/1976 | Gindler | 252/408 |
| 3,964,974 | 6/1976 | Banauch et al. | 195/103.5 C |
| 3,979,447 | 9/1976 | Bernt et al. | 260/518 R |
| 3,986,931 | 10/1976 | Bernt et al. | 195/103.5 R |
| 4,019,961 | 4/1977 | Klose et al. | 195/103.5 R |
| 4,049,702 | 9/1977 | Bernt et al. | 260/501.12 |
| 4,072,627 | 2/1978 | Gindler | 252/408 |
| 4,087,331 | 5/1978 | Bucolo et al. | 195/99 |
| 4,102,646 | 7/1978 | Sleeter | 23/230 |
| 4,125,377 | 11/1978 | Gindler | 23/230 B |
| 4,162,979 | 7/1979 | Wahlefeld et al. | 210/282 |
| 4,184,848 | 1/1980 | Batz et al. | 23/230 B |
| 4,207,203 | 6/1980 | Gindler | 252/408 |
| 4,229,527 | 10/1980 | Ziegenhorn et al. | 435/11 |
| 4,239,495 | 12/1980 | Gindler | 23/230 B |
| 4,239,649 | 12/1980 | Gindler et al. | 252/408 |
| 4,241,179 | 12/1980 | Madappally et al. | 435/16 |
| 4,242,446 | 12/1980 | Madappally et al. | 435/15 |
| 4,246,133 | 1/1981 | Gindler | 252/408 |
| 4,273,556 | 6/1981 | Gindler | 23/230 B |
| 4,274,832 | 6/1981 | Wu | 435/11 X |
| 4,276,376 | 6/1981 | Hundt et al. | 435/17 |

FOREIGN PATENT DOCUMENTS 7709175 2/1979 Netherlands.

OTHER PUBLICATIONS

Banauch et al. "Eine Glucose-Dehydrogenase fur die Glucose-Bestimmung in Korperflussigkeiten", *Z. Klin. Chem. Klin. Biochem.* pp. 1–15.

Metzger et al. "Subcellular Distribution and Properties of Heptaic Glucose Dehydrogenases of Selected Vertebrates" *Journal of Biological Chemistry*, vol. 240, No. 7, Jul. 1965, pp. 2767–2771.

Miwa et al. "Mutarotase Effect on Colorimetric Determination of Blood Glucose with Beta-D-glucose Oxidase", *Clinica Chimica Acta* vol. 37, (1972) pp. 538–540.

Hyun et al. "Purification and Properties of Pancreatic Juice Cholesterol Esterase", *The Journal of Biological Chemistry*, vol. 244, No. 77 (1969) pp. 1937–1945.

Chem. Abstracts 88: 83042f(1978) (referencing Chemical Analysis (Warsaw) 1977, 22 (1), pp. 27–35, "Optimization of the Spectro-Photometric Multi-Component Analysis".

T. K. J. Luderer, "An Automated Method for the Enzymatic Determination of Triglycerides in Serum", May 1975.

Banauch, et al., "A Glucose Dehydrogenase for the Determination of Glucose Concentations in Body Fluids", *Z. Klin. Chem. Klin. Biochem.* 13 J.G. 1975, S. 101–107 (German copy).

Kageyama, N., "A Direct Colorimetric Determination of Uric Acid in Serum and Urine with Uricase-Catalase System", *Clinica Chimica Acta*, 31: 421–426 (1971).

Stearns, E. I., "The Practice of Absorption Spectrophotometry", Wiley-Interscience, N.Y.

Wahlefeld, A. W. "Triglycerides: Determination After Enzymatic Hydrolysis", pp. 1831 et seq. H. U. Bergmeyer (ed.) *Methods of Enzymatic Analysis* (2d Eng. ed.).

Mann and Yoe, *Anal. Chem.*, 20:202 (1956).

Gindler and King, *Am. J. Clin. Pat.*, 58: 376 (1972).

"Albumin" (Trade literature), (Source and date unknown).

"Total Protein (Biuret Reagent)", Worthington, Sep. 1976.

"System Glucose", E. Merck (Darmstadt), (date unknown).

"Triglycerides fully enzymatic (neutral fat)", Boehringer Mannheim, GMBH, (date unknown).

"Cholesterol, Enzymatic Color Test", Boehringer Mannheim GMBH, (1974).
Calbiochem Catalogue (Clinical and Diagnostics) 1974, pp. 45–47, 79–97, 98–99.

*Primary Examiner*—Sidney Marantz
*Attorney, Agent, or Firm*—Woodcock, Washburn, Kurtz, Mackiewicz & Norris

[57] ABSTRACT

Method, kits and reagents for the simultaneous, kinetic spectrophotometric analysis of blood serum samples for multiple components. Pairs of components which may be simultaneously analyzed are: cholesterol and triglyceride; glucose and urea; uric acid and gamma glutamyl transferase; calcium and magnesium; albumins and total protein.

21 Claims, No Drawings

SIMULTANEOUS, KINETIC, SPECTROPHOTOMETRIC ANALYSIS OF BLOOD SERUM FOR MULTIPLE COMPONENTS

CROSS-REFERENCE TO RELATED APPLICATIONS

The present application is a continuation in part of my prior copending application Ser. No. 130,078, filed Mar. 13, 1980, now abandoned, which in turn is a continuation of Ser. No. 012,859, filed Feb. 16, 1979, now abandoned, each of which application is hereby specifically incorporated by reference.

BACKGROUND OF THE INVENTION

The present invention relates generally to the field of spectrophotometric analysis of blood serum samples, and more particularly, to the field of kinetic and end point spectrophotometric determinations of triglycerides, cholesterol, calcium, magnesium, glucose, urea, albumin, total proteins, gamma-glutamyl transferase, and uric acid.

It has long been known that blood serum may be spectrophotometrically analyzed by combining a serum sample with one or more selected reagents which will colorimetrically combine with a selected component within that sample. Upon a subsequent spectrophotometric analysis of that sample, the concentration of that component within that sample may be determined.

More recently, it has been suggested that multiple component end point determinations may be made within a single reaction medium. For example, in Chem Abstracts 88 (1978) 83042, (referencing Chemical Analysis (Warsaw) 1977, 22(1), 27-35, entitled "Optimization of the Spectrophotometric Multi-Component Analysis. The Use of a Complex Colorimetric Reagent."), it is suggested that a reagent be composed of two or more compounds may be reacted with two or more of the components of a test solution to give two colored products. The analysis procedure may be simplified if the reagent also includes all auxiliary compounds used in analysis, as for example, buffers, masking agents, etc. The optimization scheme disclosed in this abstract includes the selection of preferred conditions of analysis; that is, preferred colorimetric reagent compositions and preferred wavelengths suited for use during a certain multi-component spectrophotometric analysis. In particular, this abstract discloses a reagent composed of murexide, calmagite, and other materials for the detection of both calcium and magnesium in a given serum sample.

It has also been proposed to make kinetic determinations of the enzymatic activities exhibited by a plurality of enzymes contained in a single aqueous reaction medium. In accordance with this proposed method, known quantities of substrates, one of which is "consumed" by each of the enzymes to be determined, and any reagents required for the measurement of substrate or reaction product concentrations at preselected wavelengths may be added to the reaction medium and as employed permit enzymatic reactions to proceed simultaneously under the same reaction conditions. By sequentially measuring changes in the absorbance or fluorescence of the reaction medium over time at said wavelengths, the concentration of a corresponding number of enzymes may be determined by formulating simultaneous equations of the first degree. See U.S. Pat. No. 3,925,162 (Kanno). See also, U.S. Pat. No. 3,718,433 entitled "Method of Analyzing of Ammonia, Urea, and Tyrozene", which also discloses methods of simultaneously performing biuret and allatonin tests on certain solutions.

For other papers and disclosures relating to spectrophotometric analysis of various blood serum components, please refer to West German Auslegeschrift 2558536 (Offenlegunstag, July 7, 1977); Luderer, "An Automated Method for the Enzymatic Determination of Triglycerides in Serum"; Banauch, et al., "A Glucose Dehydrogenase for the Determination of Glucose Concentrations in Body Fluids", Z. Klin, Chem. Klin, Biochem., 13.JG. 1975, S. 101-107; Kageyama, N., "A Direct Colorometric Determination of Uric Acid in Serum in Urin With Uricase-Catalase System", Clinica Chemica Acta, 31 (1971), 421-426. See also, U.S. Pat. Nos. 3,907,645 (Richmond); 3,703,591 (Bucolo et al.); 3,925,164 (Beaucamp, et al.); 4,102,646 (Sleeter). Also, please refer to E. I. Stern's, "The Practice of Absorption Spectro-Photometry", Wiley-Inter Science, New York, and U.S. Pat. No. 3,899,297 (Hirschfeld).

While considerable progress in the determination of blood serum components has been made, various practical considerations have somewhat limited the success of prior art methods. Ideally, simple, low cost, reagents or reagent sets exhibiting extended shelf life are needed to cover a wide range of serum components. Such reagents or reagent sets preferably should be suitable for use with samples maintained within normal temperature ranges to produce reaction media which are readily analyzed to provide statistically significant determinations. Often, due to the differing reaction kinetics of the component specific colorimetric reactions, analysis of multiple components in a single reaction medium may require numerous, sequential photometric determinations, first for one component, and then, substantially later for a second component. Preferably such methods should minimize the number of transfers for photometric analyses to which a single medium must be subjected, to thereby facilitate rapid and reliable processing of samples to be analyzed for multiple component content.

SUMMARY OF THE INVENTION

The present invention provides novel methods utilizing novel reagents and reagent pairs which facilitate substantially simultaneous spectrophotometric analysis of multiple serum sample components contained within a single reaction medium. Carefully constituted reagents are added at preselected time inervals to given serum samples to produce reaction media which are analyzed, each at a single preselected "time" after final reagent addition for each of the various components. Where dual kinetic measurements are to be made, reagents are provided which ensure that spectrophotometric analysis may take place at a time which corresponds to times of optimal linearity in the reaction curves of both of serum sample components to be determined. Additionally, each reagent (reagent pair) is formulated to ensure that all component specific colorimetric reactions are non-interferring.

For example, applicant has found that it is possible for two different reagents to simultaneously combine with albumin in a serum sample so that a simultaneous determination at a first wavelength for total proteins (including albumin), and, at a second wavelength, for albumin alone may be effected. Similarily, with a different reagent pair, it has been found that simultaneous, dual component kinetic determinations can be made by carefully controlling the reaction kinetics of the component-specific reactions to achieve substantial linearity for each of these reactions during a single measurement period, which linearity is maintained over wide ranges of component concentrations. Additionally, the initial reagent added to each serum sample is formulated so that all non-specific reactions which might otherwise cause false or inaccurate readings are permitted to occur in advance of the measurement period. Accordingly, the present invention provides novel reagents, reagent sets and methods which enable substantially simultaneous, dualwavelength analyses to be performed on a single reaction medium to reliably quantify the concentrations of at least two sample components contained within that reaction medium.

A primary object of the present invention is the provision of a method which permits substantially simultaneous spectrophotometric analysis of two blood serum components in a single reaction medium.

A further object of the present invention is the provision of a method for substantially simultaneously spectrophotometrically determining the concentrations of triglycerides and cholesterol in a blood serum sample.

A further object of the present invention is the provision of a method for simultaneously spectrophotometrically determining the concentrations of calcium and magnesium in a given blood serum sample.

A further object of the present invention is the provision of a method for simultaneously spectrophotometrically determining the concentrations of glucose and urea contained within a given blood serum sample.

A further object of the present invention is the provision of a novel method for simultaneously spectrophotometrically analyzing a blood serum sample to determine the concentrations of albumin and total proteins contained therein.

Another object of the present invention is the provision of reagents and a novel method for analyzing a single blood serum sample to determine the concentrations of gammaglutamyl transferase and uric acid contained therein.

These and further objects of the present invention will become apparent from the following more detailed description.

DETAILED DESCRIPTION OF THE PREFERRED EMBODIMENT

From the following description of various embodiments of the present invention, one of ordinary skill in this art will appreciate that various modifications or variations can be made to the reagents and methods described hereinafter without departing from the scope of the present invention, which is more particularly defined in the appended claims.

In accordance with the preferred embodiment of the present invention, reagents, reagent sets and methods are provided for use in simultaneously determining triglycerides-cholesterol, calcium-magnesium, glucose-urea, albumin-total protein, and gamma-GT-uric acid. Since separate reagents/reagent sets and methods are used in determining each of the above identified component pairs, such reagents and methods will be treated substantially separately in the following description, however, one of ordinary skill in this art will readily recognize the similarities and differences pertaining to the hereinafter described pair determination methods and reagents.

1. Simultaneous Determination of Cholesterol-Triglycerides In a Single Blood Serum Sample.

In accordance with the cholesterol-triglyceride embodiment of the present invention, a three reagent kit is provided to the reagent user. This kit is formulated to maximize the shelf life and effectiveness of the various reagent components by separating one of the reagents used during the sample testing procedure into separate portions (Reagents $A_1$ and $A_2$) for mixing prior to use. Thus, Reagent Solutions $A_1$ and $A_2$ should be combined and permitted to incubate for approximately 10 minutes at 35° C. to produce a composite reagent solution (Reagent A). This composite reagent solution (Reagent A) will retain its effectiveness for at least several hours, and as long as several days. In order to perform the desired cholesterol-triglyceride determinations, approximately 1 ml of composite reagent solution (Reagent A) per 20 microliters of serum sample is added to that sample, and incubated from between 10 to 20 minutes, preferably 13 to 15 minutes, or ideally about 14 minutes, at 37° C. The addition of the composite reagent solution (Reagent A) begins a colorimetric reaction between cholesterol present in the serum sample and the composite reagent solution.

In order to produce an accurate cholesterol determination, however, it is important that the reaction proceed substantially linearly during subsequent analysis, so that in analyzing for the concentration of cholesterol, the rate of change of concentration of the cholesterol specific complex, (3,5 diacetyl-1,4-dihydrolutidine), which is as analyzed at about 405 nm, will be indicative of the amount of cholesterol originally present in the serum sample. The reaction pathway utilized to obtain the colorimetrically active cholesterol complex is generally described by Röschlau, P., et al., *Z. Klin. Chem. Klin. Biochem.* 12 (1974) 226. The particular concentrations chosen now are used in order to ensure early linearity, i.e. linearity during the analyses period chosen.

In accordance with this embodiment of the present invention, the composite reagent solution (Reagent A) initially added to the serum sample additionally comprises various enzymes and other components which do not participate in colorimetric cholesterol reaction pathway referred to above, but rather are components which comprise some of the materials necessary to conduct an enzymatic determination of triglycerides utilizing a pathway similar to that disclosed by Wahlefeld, A. W. (1974), "Triglycerides. Determination After Enzymatic Hydrolysis", page 1831ff in H. U. Bergmeyer, Editor, *Methods of Enzymatic Analysis*, second English edition. In accordance with the method of this embodiment, during the initial stages of the colorimetric cholesterol reaction, the enzymes and other components which will be active in the triglyceride determination are inactive, except the hydrolyzing enzymes, since the addition of glycerol kinase is necessary in order to begin the reaction sequence which results in a colorometrically active triglyceride complex having an absorption maximum (showing decreasing absorptions) at 340 nm. Accordingly after the aforementioned 14 minute incubation period, a 30 U/ml glycerol kinase solution (Reagent B) is added at a volumetric ratio of 1:50 (Reagent B:Reagent A) to the reaction medium, whereupon the resulting reaction medium is immediof phenol red (also an increasing absorption value) at 546 nm. By beginning these measurements at 20 to 30 seconds after the addition of Reagent E, linearity for both glucose and urea are obtained, provided concentrations of the serum fall within normal diagnostic ranges. In Reagents D and E, as described above, enzyme concentrations are carefully selected in order to permit kinetic measurement of substrate concentrations, while nonetheless ensuring that the enzymatic reactions will not proceed so rapidly that they have been completed prior to the end of the reaction period. It has further been determined that, by utilizing the above described reagent pair, the urea and glucose reactions permitting this spectrophotometric determination are non-interferring, and provide reliable, accurate results.

To ensure proper stability of the Reagents D and E but nevertheless the timely initiation of each of the reactions, both Reagent D and Reagent E contain components required for each of the reactions. That is, neither Reagent D or Reagent E are a complete system for either determination.

4. Simultaneous Spectro-Photometric Determination of Serum Samples for Albumins and Total Proteins.

Heretofore, reagents permitting the simultaneous determination of albumin and total proteins in a single reaction medium have not been known. Since albumin is a protein, one might expect that any reagent which colorimetrically combines with total proteins to permit spectrophotometric analysis might necessarily inhibit one of those proteins, albumin, from combining with any reagent which is albumin specific. It has been determined, however, that when the Biuret total protein method and HABA Dye method are combined as described hereinafter, simultaneous determinations of total proteins and albumin may be effected. It is theorized that albumin possesses at least two reaction sites which are independent, non-interferring reaction sites permitting spectrophotometric determination of albumin at two wavelengths, a first wavelength of 560 nm at which total proteins are determined, and a second wavelength of 482 nm at which a colorimetric, albumin-specific complex is determined.

The novel reagent for use is performing the above described albumin-total protein test should consist essentially of the following solution:

0.3 mmol/l 2-(4'-hydroxybenzeneazo)-benzoic acid $C_{13}H_{10}N_2O_3$)
0.1 mol/l sodium hydroxide (NaOH)
41 mmol/l potassium-sodium tartrate ($KNaC_4H_4O_6.4H_2O$)
9 mmol/l copper sulfate ($CuSO_4.5H_2O$)
15 mmol/l potassium iodide (KI)

which is used to carry out the reactions at a preferred temperature of about 37° C.

5. Simultaneous Spectrophotometric Analysis of Serum Samples for Gamma-Glutamyl Transferase and Uric Acid In accordance with the present invention, a novel reagent and method are provided for simultaneously analyzing a serum sample to determine its gamma-glutamyl transferase and uric acid contents. For gamma-glutamyl transferase determination, a pathway similar to that disclosed by G. Szasz Z. Klin. Chem. u Klin. Biochem. 12, 228 (1974) is utilized. See also Szasz, "Methoden der enzymatischen Analyse I" (H. U. Bergmeyer, publisher); Auflage, page 757, Verlag Chemie, Weinheim/Bergstrasse (1974). The reaction sequence used to determine the concentration of uric acid utilizes the PAP method (Trinder), which relies upon reactions involving phenol and 4-amino phenazon. See also, Kageyama, "A Direct Colorimetric Determination of Uric Acid in Serum and Urine with UricaseCatalase System", Clin. Chim. Acta., 31 (1971) 421–426.

In accordance with the method of the present invention, simultaneous determinations of uric acid and gamma-glutamyl transferase are accomplished by adding an initial reagent, Reagent F, which comprises all components necessary to carry out the dual analysis, except L-gamma-glutamyl-3-carboxy-4-nitro anilide, which is a material which triggers the gamma-glutamyl transferase reaction pathway. This Reagent F should be prepared as a solution consisting essentially of:

100 mmol/l tris-hydroxymethylaminomethane (buffer pH 8.25)
100 mmol/l glycylglycine
9 mmol/l phenol
3 U/ml peroxidase (E.C. 1.11.1.7)
180 U/l uricase (E.C. 1.7.3.3)
25 micromol/l 4-amino-phenazon In the above solution, the amount of peroxidase and uricase utilized in the subject solution can vary by a ±5%.

In accordance with the method of the present invention, 1 ml of Reagent F should be measured at a wavelength of 505 nm to determine a base value. 100 microliters of the sample should then be added to 1 ml of this reagent, and the sample should be permitted to incubate for at least 7 minutes at 37° C. Then, 100 l microliters of a 45 mmol/l solution of L-gamma-glutamyl-3-carboxy-4-nitro anilide (Reagent G) should be added to the reaction mixture, after which simultaneous measurements of the absorbances at 505 nm and the [delta] A/minute at 405 nm should be taken, the former to determine the uric acid concentration, and the latter to provide a measure of the gamma-glutamyl transferase activity. Additionally, for the uric acid determination, a serum blank should be taken into account.

As seen from the above, simultaneous determinations for uric acid and gamma-glytamyl transferase are possible by reason of the use of a reagent pair which permits stabilization of the serum sample and starting of the uric acid specific reaction substantially in advance of the addition of the triggering component necessary to begin the gamma-glytamyl transferase specific reaction, whereby it is possible to simultaneously determine the uric acid end point and the [delta] A/minute of gamma-glytamyl transferase activity.

SUMMARY OF THE PREFERRED EMBODIMENTS

As seen from the above, extremely simple and economical reagents are provided which enable the simultaneous analysis of a serum sample to determine the concentrations of two components contained therein. In accordance with the preferred embodiments, dual spectrophotometric determinations are made within a single analysis period using a dual wavelength spectrophotometric. Preferably, such a spectrophotometric should rapidly operate between two alternate wavelengths to perform a substantially simultaneous evaluation of a given reaction medium at said wavelengths. For example, in the preferred embodiment, a spectrophotometer capable of making 52 spectrophotometric determinations per second, 26 determinations per second for each ately and substantially simultaneously analyzed at 340 nm and 405 nm to determine the concentrations of triglycerides and cholesterol, respectively.

In order to obtain improved reaction kinetics, the composite reagent solution (Reagent A) of this embodiment utilizes adenosine triphosphate (ATP) concentrations which are substantially elevated, (within the range of 0.40–0.50 mmol per liter) to decrease the reaction velocity to thereby improve the linearity of the reaction during the analysis period.

The preferred embodiment reagent mixtures which are combined to form the composite reagent are composed as follows:

A first reagent (Reagent A) is prepared by making a solution in water containing the following components:
- 0.054 to 0.056, preferably 0.055 mol/l trishydroxymethylaminomethane
- 0.032 to 0.034, preferably 0.033 mol/l hydrochloric acid
- 0.0037 mol/l magnesium nitrate
- 0.15 mol/l ammonium sulfate
- 0.55 mol/l ammonium chloride
- 1.60 mol/l methanol
- 0.021 mol/l acetylacetone and at least 1300 U/ml catalase (EC 1.11.1.6) in water. After the above solution (Reagent A) has been able to stabilize for at least 45 minutes at 35° C., and upon a prolonged period of storage if such is desired prior to performance of the desired cholesterol-triglyceride determinations, the above reagent is combined with the following reagent (Reagent $A_2$) which consists essentially of:
- at least 100 U/l cholesteroloxidase (EC 1.1.3.6)
- at least 600 U/l cholesterolesterase (EC 3.1.1.13)
- at least 6 U/ml lactatedehydrogenase (EC 1.1.1.27)
- at least 1 U/ml pyruvatekinase (EC 2.7.1.40)
- at least 80 U/ml lipase (EC 3.1.1.3)
- 0.2 mmol/l nicotineamide adeninedinucleotide (in reduced form, NADH)
- 0.40 to 0.50, preferably 0.44 mmol/l adenosine triphosphate
- 0.36 mmol/l phosphoenolpyruvate 0.1% hydroxypolyethoxydodecane As mentioned above, the two above described reagents are combined and permitted to stabilize for a period of at least about 10 minutes prior to the commencement of testing. While utilizing both ammonium sulfate and ammonium chloride in Reagent A, a sufficient sulfate ion concentration has been ensured to activate the latter-added glycerol kinase. In this manner, premature precipitation in the composite reagent solution is nonetheless prevented, while ensuring immediate glycerol kinase activity upon addition of the following reagent, Reagent B, to the reaction medium which comprises Reagent A and the serum sample (37° C.). The prepared solution of glycerol kinase (Reagent B) includes:
- 1 mol/l ammonium sulfate
- 30 U/ml gylcerol kinase (EC 2.7.1.30)

As seen from the above, an extremely simple yet reliable reagent set is disclosed, together with a method for using same, which enables a given serum sample to be simultaneously kinetically analyzed for its concentrations of triglycerides and cholesterol.

2. Simultaneous Photometric Analysis of Serum Sample for Calcium and Magnesium.

In accordance with the method of the present invention, a single reagent (Reagent C) is prepared utilizing a solution containing the following components:
- 0.156 mmol/l xylidyl blue I
- 25.0 mmol/l boric acid
- 25.0 mmol/l potassium chloride
- 21.95 mmol/l sodium hydroxide
- 0.23 mmol/l methylthymol blue, the above components being mixed in a water-ethanol mixture (50 vol % ethanol).

Applicants have found that the above composite reagent, which is based on a combination of reagents previously available for individual determinations of magnesium and calcium, more particularly the methods disclosed by Mann and Yoe, Anal. Chem. 20, 202 (1956) and Gindler and King, Am. J. Clin. Pat. 58, 376, (1972), produce non-interferring reactions wherein end point determinations for the magnesium-xylidyl blue complex at 505 nm and calcium-methylthymol blue at 618 nm may be taken at 25° C. after an incubation period of 5 minutes following an addition of 1 ml of reagent per 10 microliters of sample.

3. Simultaneous Spectrophotometric Analysis of Serum Samples for Glucose and Urea.

In accordance with the method of the present embodiment, an initial reagent (Reagent D) is added to a given serum sample and permitted to incubate with that sample for a period of time sufficient to prevent false negatives, to stabilize the solution, and to allow the completion of all non-specific reactions which occur between the components of Reagent D and the serum sample. In accordance with the method of the present invention, the reaction pathways utilized to accomplish spectrophotometric determinations for urea are similar to those disclosed by the Harleco Company relating to blood urea nitrogen, and/or of the E. Merck Company of Darmstadt. See for example Von D. Banauch, et al., "A Glucose Dehydrogenase for the Determination of Glucose Concentrations In Body Fluids", Z. Klin. Chem. Klin. Biochem. 13.Jg. 1975, S. 101–107. Reagent D is prepared by preparing a solution consisting essentially of:
- 0.11 mmol/l phenol red (buffered, such as Harleco Art. No. 81350A), buffered to a pH of about 7.04.
- 600 U/l ± 10% glucose dehydrogenase (EC 1.1.1.47)
- 12.6 U/l mutarotase (EC 5.1.3.3)

A Reagent E is obtained by preparing a solution consisting essentially of:
- 23.3 kU/l ± 10% urease (EC 3.5.1.5)
- 0.65 mmol/l nicotinamide adenine dinucleotide (NAD)
- 154 mmol/l sodium chloride In accordance with the preferred method of this embodiment, 1 ml of Reagent D is added per 30 microliters of serum sample. After an incubation period of at least about 2 minutes, at 25° C., Reagent E is added at a ratio of 50 microliters of Reagent E to each ml of previously added Reagent D. The glucose determination is then conducted during an analysis period which begins between 20 to 30 seconds after the addition of Reagent E through the measurement of absorption maximum of NADH (an increasing absorption value) at 340 nm. The urea determination may also be made during this reaction period by measurement of the absorption maximum wavelength, is preferred. As used herein, the word "simultaneous" may include applications wherein determinations at two different wavelengths occur at intervals no greater than about 10 seconds apart, and preferably less than 1 second apart.

Further, one or ordinary skill in this art will recognize that while specific proportions have been provided relating to certain of the components of the above described reagents, certain of those components may be used in altering proportions without substantially affecting the reaction kinetics within the reaction medium. One of ordinary skill in the art will further recognize, in view of the above description, however, that except as otherwise indicated, specific proportions of other components, particularly the above mentioned enzymes, cannot be substantially altered without affecting the reaction kinetics in the reaction sample. Further, while three of the above mentioned examples refer to 37° C. and the other two 25° C. as the reaction temperatures, those of ordinary skill in the art will recognize that departures from this temperature will result in alterations in the reaction kinetics, and thus the possibility that the time periods specified in the above examples may need to be shortened or lengthened from the periods set forth above in order to accommodate a normal range of component concentrations.

I claim:

1. A method for carrying out the substantially simultaneous spectrophotometric analysis of blood serum samples for multiple components, contained within a single reaction medium, comprising the steps of:
   (a) adding a first reagent mixture to initiate a colorimetric reaction with at least one of said components to be analyzed, to produce a first reaction mixture;
   (b) incubating said first reaction mixture for a preselected length of time;
   (c) adding a second reagent to initiate at least one additional colorimetric reaction with at least a second sample component to produce a second reaction mixture;
   (d) incubating said second reaction mixture for a preselected length of time; and
   (e) substantially simultaneously spectrophotometrically analyzing said second reaction mixture at a plurality of wave lengths to at least determine the presence of said components in said serum sample; said spectrophotometric analysis of step (e) being a kinetic analysis of at least one of said colorimetric reactions, and comprising the kinetic analysis of a plurality of said colorimetric reactions, the incubation times of steps (b) and (d) being selected so that substantial kinetic linerarity will be exhibited by said colorimetric reactions during the performance of step (e), and said components comprising at least cholesterol and trigylceride, and said fist colorimetric reaction being a cholesterol specific colorimetric reaction.

2. The method of claim 1 wherein said cholesterol specific reaction produces 3,5-diacetyl-1,4-dihydrolutidine and wherein at least one of said wave lengths is about 405 nm.

3. A method for carrying out the substantially simultaneous spectrophotometric analysis of blood serum samples for multiple components, contained within a single reaction medium, comprising the steps of:
   (a) adding a first reagent mixture to initiate a colorimetric reaction with at least one of said components to be analyzed, to produce a first reaction mixture;
   (b) incubating said first reaction mixture for a preselected length of time;
   (c) adding a second reagent to initiate at least one additional colorimetric reaction with at least a second sample component to produce a second reaction mixture;
   (d) incubating said second reaction mixture for a preselected length of time; and
   (e) substantially simultaneously spectrophotometrically analyzing said second reaction mixture at a plurality of wave lengths to at least determine the presence of said components in said serum sample; said spectrophotometric analysis of step (e) being a kinetic analysis of at least one of said colorimetric reactions, and comprising the kinetic analysis of a plurality of said colorimetric reactions, the incubation times of steps (b) and (d) being selected so that substantial kinetic linerarity will be exhibited by said colorimetric reactions during the performance of step (e), and said components comprising cholesterol and trigylceride, and said second of said reagents initiating a triglyceride colorimetric reaction.

4. The method of claim 3 wherein said triglyceride specific reaction produces a colorimetrically active triglyceride complex having an absorption maximum showing decreasing absorptions at 340 nm.

5. A method of simultaneously spectrophotometrically analyzing blood serum samples for multiple components, within a single reactions medium, comprising the steps of:
   (a) mixing said blood serum sample with a first reagent containing materials sufficient to initiate nonspecific, false negative producing reactions but insufficient to initiate a component specific colorimetric reaction;
   (b) incubating said mixed solution for a preselected length of time;
   (c) adding a second reagent solution sufficient to initiate at least two component specific colorimetric reactions;
   (d) further incubating said solution for a preselected period of time; and
   (e) spectrophotometrically analyzing the product of step (d) at at least two different wave lengths to determine the presence of at least a plurality of components contained within said serum sample, said component specific reactions being glucose and urea specific reactions.

6. The method of claim 5 wherein said second solution comprises urease, and NADH.

7. A method of simultaneously spectrophotometrically analyzing blood serum samples for multiple components, within a single reactions medium, comprising the steps of:
   (a) mixing said blood serum sample with a first reagent containing materials sufficient to initiate nonspecific, false negative producing reactions but insufficient to initiate a component specific colorimetric reaction;
   (b) incubating said mixed solution for a preselected length of time;
   (c) adding a second reagent solution sufficient to initiate at least two component specific colorimetric reactions;
   (d) further incubating said solution for a preselected period of time; and (e) spectrophotometrically analyzing the product of step (d) at at least two different wave lengths to determine the presence of at least a plurality of components contained within said serum sample, said first reagent solution comprising phenol red, glucose dehydrogenase, and mutarotase.

8. The method of claim 7 wherein said component specific reactions determine the concentrations of glucose within said reaction mixture by spectrophotometrically analyzing the absorption maximum of NADH (an increasing absorption value) and of urea through the measurement of the absorption maximum of phenol red (also an increasing absorption value).

9. A method for analyzing blood serum samples for multiple components, contained within a single reaction medium, comprising the steps of:
(a) mixing said serum sample with a first reagent solution to initiate a colorimetric reaction with at least one of said components to be analyzed, to produce an initial reaction mixture;
(b) incubating said initial reaction mixture for at least a preselected period of time to permit the completion of said colorimetric reaction;
(c) adding a second reagent solution to said initial reaction mixture to initiate at least one additional colorimetric reaction with at least a second sample component to produce a final reaction mixture;
(d) incubating said final reaction mixture for a preselected period of time; and
(e) substantially simultaneously spectrophotometrically analyzing said final reaction mixture at a plurality of wave lengths to determine the presence of said components in said serum sample; said spectrophotometric analysis of step (e) being an end point analysis of the colorimetric reaction product produced by steps (a) and (b), and a kinetic analysis of the colorimetric reaction product produced by steps (c) and (d), and the incubation period of step (c) being selected so that substantial kinetic linearity will be exhibited by said colorimetric reactions during the performance of said kinetic analysis, said components comprising at least uric acid and gamma glutamyl transferase.

10. The method of claim 9 wherein said first reagent initiates said uric acid specific colorimetric reaction.

11. The method of claim 10 wherein said plurality of wave lengths are about 505 nm and 405 nm.

12. A reagent kit for use in carrying out the substantially simultaneous spectrophotometric determination of cholesterol and triglycerides in a given serum sample, comprising a first glycerol kinase containing solution, a second, catalase containing solution, and a third enzymatic reagent solution containing at least those components which, when combined with said first and second solutions, initiate cholesterol and triglyceride specific colorimetric reactions, whereby said solutions may be stored for extended periods of time prior to use.

13. The kit of claim 12 wherein said first solution consists essentially of a mixture of glycerol kinase and ammonium sulfate.

14. The kit of claim 12 wherein said third solution comprises cholesterol oxidase, cholesterol esterase, lactate dehydrogenase, pyruvate kinase, nicotinamide adeninedinucleotide, adenosine triphosphate, and phosphoenol pyruvate.

15. The kit of claim 12 wherein said third solution comprises a cholesterol oxidizing agent.

16. The kit of claim 12 wherein said second and third solution comprise all the components necessary to initiate a colorimetric, cholesterol specific reaction.

17. The kit of claim 12 wherein glycerol kinase, adenosine triphosphate and sulfate ions are each present in different ones of said three solutions, whereby combination of all of said three solutions is necessary to said initiation of said triglyceride specific colorimetric reaction.

18. The kit of claim 12 wherein said second solution comprises ammonium sulfate and ammonium chloride.

19. The kit of claim 18 wherein said second solution further comprises magnesium nitrate, hydrochloric acid, and trishydroxymethylaminomethane.

20. A reagent for the simultaneous spectrophotometric analysis of serum samples for calcium and magnesium, consisting essentially of effective amounts of: xylidyl blue, boric acid, potassium chloride, sodium hydroxide, and methylthymol blue, in an aqueous alcohol solution.

21. A method of simultaneously determining albumins and total protein contained within a given serum sample comprising the step of simultaneously mixing said serum sample with biuret and haba reagents, incubating the resultant mixture, and substantially simultaneously spectrophotometrically determining the concentrations of albumin and total protein within said reaction mixture.

* * * * *